United States Patent [19]

Zimmerman et al.

[11] Patent Number: 4,897,394

[45] Date of Patent: Jan. 30, 1990

[54] ANTIVIRAL COMBINATIONS

[75] Inventors: Thomas P. Zimmerman; Gerald Wolberg, both of Cary, N.C.

[73] Assignee: Burroughs Wellcome CO., Research Triangle Park, N.C.

[21] Appl. No.: 8,627

[22] Filed: Jan. 29, 1987

[30] Foreign Application Priority Data

Jan. 30, 1986 [GB] United Kingdom ................. 8602346

[51] Int. Cl.$^4$ ................... A61K 31/505; A61K 31/52
[52] U.S. Cl. .................................... 514/258; 514/262
[58] Field of Search ............................... 514/262, 258

[56] References Cited

PUBLICATIONS

Chemical Abstracts 84:174042q (1976).
Chemical Abstracts 85:37239r (1976).
Chemical Abstracts 108:101366c (1988)
The Merck Index, 10th Ed., Merck & Co., Inc., Rahway, N.J., 1983, p. 138 (No. 140).

Primary Examiner—Jerome D. Goldberg
Attorney, Agent, or Firm—Donald Brown

[57] ABSTRACT

This invention relates to synergistic combinations of nucleoside analogues, which are converted to viral DNA polymerase inhibitors through the action of at least one virus-induced enzyme, and nucleoside transport inhibitors. These combinations are especially useful in combatting herpes virus infections.

1 Claim, No Drawings

ANTIVIRAL COMBINATIONS

The present invention relates to new antiviral combinations for the chemotherapeutic treatment of virus infections, especially viruses of the herpes group.

During the last ten years or more various antiviral chemotherapeutic agents have been developed for clinical evaluation. A problem with the development of such agents is that, unlike bacteria, viruses are not free living organisms but are dependent for replication on the life processes of the host cell which they are infecting. It is therefore highly desirable for the antiviral agent to exert its effect specifically on the replicative processes of the virus rather than on the corresponding processes of normal (non-infected) cells. The antiviral agents so far developed act via a variety of mechanisms to exert their antiviral effect, such mechanisms involving inhibition of different stages in the process of viral replication in the host cells.

One particular stage of replication at which the virus is susceptible to inhibition is the stage of nucleic acid replication. In the case of DNA viruses, the production of new viral DNA involves the interaction of the enzyme DNA polymerase with the constituent nucleotides (specifically desoxyribonucleotides) which act as building blocks for the new DNA. Antiviral action at this stage generally involves the metabolism of nucleoside analogues to "fraudulent" or deleterious nucleotides which mimic the normal viral materials and either compete for DNA polymerase or are incorporated into the viral DNA chain to make it non-functional. These "fraudulent" or deleterious nucleotides comprise a nucleoside triphosphate derived from a nucleoside analogue which is converted by enzymes first into the monophosphate and then subsequently into the diphosphate and finally into the triphosphate. An example of this type of antiviral is acyclovir (i.e. 9-[(2-hydroxyethoxy)methyl]guanine) which is related to the naturally occurring nucleoside, guanosine, but which contains an acyclic side-chain in the 9-position compared with a cyclic sugar residue in this position in guanosine. The antiviral mechanism of action of acyclovir involves first its permeation of the cell membrane and then its conversion to acyclovir monophosphate by the virally specified enzyme thymidine kinase. Once formed, acyclovir monophosphate is converted by normal cellular enzymes (kinases) to the diphosphate and subsequently to acyclovir triphosphate (ACVTP). Acyclovir triphosphate serves as an inhibitor of viral DNA polymerase since it resembles the natural nucleotide substrate, deoxyguanosine triphosphate (dGTP), and as a result competes with dGTP for binding to the DNA polymerase and thus competitively inhibits the effectiveness of the enzyme and consequently viral replication. When ACVTP acts as a substrate for DNA polymerase it becomes incorporated into the viral DNA chain but since it lacks the 3'-hydroxy group of the cyclic sugar moiety it acts as a DNA chain terminator. It also apparently inactivates the viral DNA polymerase. Viral replication is thereby prevented.

Thus, the antiviral effect of acyclovir, and related compounds which operate via an analogous mode of action, involves competitive inhibition and apparent inactivation of the viral DNA polymerase. A disadvantages aspect of a competitive inhibitor is that the competing substrate for the particular enzyme in question may accumulate and thereby antagonize the binding of the inhibitor. In this manner, the buildup of, for example, thymidine may hinder the binding of acyclovir to the virally specified thymidine kinase and thereby antagonize the subsequent phosphorylation of acyclovir, which phosphorylation has been shown to be an essential step for the antiviral action of this drug.

We have now discovered that the use of a nucleoside transport inhibitor in conjunction with an antiviral agent of the above described type surprisingly does not affect the levels of the antiviral agent in the cell despite decreasing the influx into the cell of naturally occurring nucleosides, e.g., thymidine. We believe this is due to the restriction by the nucleoside transport inhibitor of the influx of physiologically occurring nucleosides, and hence the ratio of the antiviral compound to the competing nucleoside substrate of the virally specified thymidine kinase is greatly improved. The phosphorylation of the antiviral compound is thus enhanced.

The net result is that the use of a nucleoside transport inhibitor in combination with an antiviral agent of the above described type results in a surprising synergistic increase in antiviral efficacy in comparison with the individual antiviral effects of the components of the combination. Indeed, nucleoside transport inhibitors may exhibit no antiviral effect whatsoever. It is particularly surprising that inhibitors of nucleoside transport should potentiate the activity of the antiviral compounds of the invention as such antiviral compounds would be expected to gain entry to cells by the same route as naturally occurring nucleosides, owing to their structural similarity. Thus, it could be expected that the antiviral compounds should also be inhibited from gaining access to the cells. However, it has now been found that this is not the case.

According to a first feature of the present invention there is provided a combination of (a) an antiviral compound which is converted in vivo by a virus-induced enzyme to an inhibitor of, and/or an alternative substrate for, a viral DNA polymerase, and (b) a nucleoside transport inhibitor, components (a) and (b) of the combination being employed in a ratio whereby a synergistic antiviral effect is achieved.

The term "synergistic antiviral effect" is used to denote an antiviral effect which is greater than the predicted additive effects of the individual above-defined components of the combination.

According to a second feature of the invention there is provided a combination as described above for use in medical therapy, particularly for the treatment of herpes virus infections, especially herpes simplex, varicella zoster, cytomegalovirus (CMV) and Epstein-Barr virus (EBV) infections.

In a yet further feature of the present invention there is provided the use of a combination as described above in the manufacture of a medicament for the treatment of herpes virus infections. The invention further provides a method for the treatment of viral diseases in a human or animal body which comprises administering to the human or animal body an effective amount of a combination as defined above. It will be appreciated that in accordance with the present invention the antiviral compound and the nucleoside transport inhibitor may be administered simultaneously or sequentially, or even by different routes. In the latter case, however, the components of the combination are administered within a sufficiently short interval to ensure that a synergistic antiviral effect is achieved.

The present invention also provides a method of potentiating in a mammal having a viral infection the antiviral activity of an antiviral compound being administered to said mammal and which depends on a viral-induced enzyme for conversion to a deleterious substrate and/or inhibitor of viral DNA polymerase which comprises administering to said mammal an effective, non-toxic potentiating amount of a nucleoside transport inhibitor simultaneously with, previous to or subsequent to the administration of the antiviral compound.

An advantage of the combination according to the invention is that it enables one to obtain an improved antiviral efficacy at a particular dosage of the antiviral compound (compared with the compound used alone) thereby improving the therapeutic index of the compound. Thus, for example, the combination may be used to treat conditions which would otherwise require relatively large dosages of the antiviral compound at which toxicity problems may occur. The smaller dosages of the combination may provide for increased convenience to the patient and increased compliance. The combination according to the invention is especially applicable to the treatment or prophylaxis of herpes simplex types 1 and 2 infections, but other herpes virus infections can also be treated for example varicella zoster, cytomegalovirus and Epstein-Barr virus infections.

With regard to the antiviral compound, this can be selected from a compound of formula (I) that is phosphorylated in vivo by virus-induced enzymes. Such compounds are generally substrates for an appropriate kinase enzyme of viral origin which phosphorylates the compounds to form initially a monophosphate which is then phosphorylated (also by kinase enzymes of either viral or cellular origin) first to the disphosphate and finally to the triphosphate which serves as the DNA polymerase inhibitor. The use of an antiviral compound that is selectively phosphorylated by viral enzymes rather than by cellular enzymes provides a greater concentration of the phosphorylated material in infected cells than in non-infected cells, and thus provides a more selective antiviral effect. It is also preferred to use an antiviral compound that is not only a DNA polymerase inhibitor but is also, when incorporated into the viral DNA chain, a chain terminator and, possibly, an inactivator of the viral DNA polymerase.

Thus, for example, acyclovir, as mentioned above, is converted by virus-coded thymidine kinase (but not to any substantial extent by cellular thymidine kinase) to the monophosphate which is then converted to the triphosphate via the diphosphate by cellular enzymes. Acyclovir is also a DNA chain terminator. The mechanism of acyclovir and other antiviral nucleoside analogues is described by de Clerque in "New Trends in Antiviral Chemotherapy", Archives Internationale de Physiologie et de Biochimie, 1979, 87 (2), pages 353–395.

The antiviral compound employed in the combinatins according to the invention may be selected, for example, from acyclovir and analogues thereof, e.g., those compounds of formula

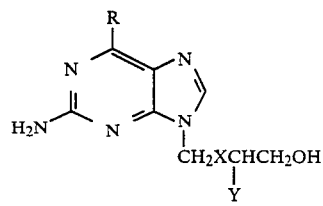

(wherein X is oxygen or sulphur, R is hydrogen, hydroxy or amino and Y is hydrogen or hydroxymethyl) and physiologically acceptable salts and esters thereof.

In addition to acyclovir, examples of preferred compounds of formula (I) for use in accordance with the present invention include 9-[[(2-hydroxy-1-(hydroxymethyl)ethoxy]methyl]guanine as well as prodrugs that are converted in vivo into the above compounds, e.g., 2-amino-9-[(2-hydroxyethoxy)methyl]adenine, 9-[[2-hydroxy-1-(hydroxymethyl)ethoxy]methyl]-2,6-diaminopurine, and 2-amino-9-[(2-hydroxyethoxy)methyl]purine.

The above-described antiviral compounds can be obtained by processes that are described in the literature for example, U.K. Patent Specifications 1523865A and 2014070A, and European Patent Specification No. 108285.

Nucleoside transport inhibitors for use in accordance with the present invention may be any non-toxic nucleoside transport inhibitor. Particularly preferred compounds of the present invention are dilazep, dipyridamole, 6-[(4-nitrobenzyl)thio]-9-($\beta$-D-ribofuranoxyl)purine, papaverine, mioflazine, hexobendine and lidoflazine or physiologically acceptable salts and esters thereof. It should be noted that these preferred compounds represent a wide variation in chemical structure while possessing the common biochemical property of nucleoside transport inhibition.

The above-described nucleoside transport inhibitors may be prepared for example as described in the following references dipyridamole (U.K. Patent Specification 807826), dilazep (U.K. Patent Specification 1107470). hexobendine (U.S. Patent Specification 3267103), lidoflazine (U.K. Patent Specification 1,055,100), mioflazine (European Patent Specification No. 0068544), papaverine (Popp F. D. and McEwen W. E., J. Am. Chem. Soc. (1957), 79, 3773–3777), 6-[(4-nitrobenzyl)thio]-9-($\beta$-D-ribofuranosyl)purine (Brajewsar P., Chen M. F., Paterson A.R.P., J. Med. Chem. (1975), 18, No. 10, 968–973).

The present invention further includes a process for preparing the above-defined combinations according to the invention which comprises bringing into association the above-defined antiviral compound and a nucleoside transport inhibitor to provide a synergistic antiviral effect. The combinations according to the invention may be administered to the subject concerned in conventional manner. As indicated above, the antiviral compound and the nucleoside transport inhibitor may be administered simultaneously (e.g., in a unitary pharmaceutical formulation) or separately (e.g., in separate pharmaceutical formulations). In general, the combinations may be administered by the topical, oral, rectal or parenteral (e.g., intravenous, subcutaneous or intramuscular) route. The dosage of the combination will depend on the condition being treated, the particular antiviral agent and nucleoside transport inhibitor concerned and other clinical factors such as the weight and condition of the patient and the route of administration of the compound. However, for administration by the oral route a dosage of the antiviral compound of 1 to 100 mg/kg/day, preferably 10 to 40 mg/kg/day, is generally sufficient. For administration by the parenteral route, a dosage of antiviral compound of 1 to 60 mg/kg/day, preferably 15 to 30 mg/kg/day is generally sufficient. The amount of nucleoside transport inhibitor in the combination will be independent of the amount of antiviral compound specified above and will be sufficient to inhibit nucleoside transport effectively and is preferably in the range of 0.1 to 100 mg/kg/day and particularly in the range 1 to 20 mg/kg/day.

The range of ratios of the antiviral compound to the nucleoside transport inhibitor for use according to this invention is from 1:100 to 100:0.1, preferably from 1:20 to 60:1.

Unit dosages, e.g., for administration four times per day, may contain from 17.5 to 1750 mg of the antiviral compound and from 1.75 to 1750 mg of the nucleoside transport inhibitor, preferably 175 to 700 mg of the antiviral compound and 17.5 to 350 mg of the nucleoside transport inhibitor.

For convenience, the antiviral compound and nucleoside transport inhibitor are preferably administered in a unitary pharmaceutical formulation. Thus, the present invention further provides a pharmaceutical formulation comprising an antiviral compound as defined above in accordance with the invention, and a nucleoside transport inhibitor, together with at least one pharmaceutical carrier or excipient, the antiviral compound and nucleoside transport inhibitor being present in the formulation in a ratio whereby a synergistic antiviral effect is achieved upon administration to a human or animal subject.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by conventional pharmaceutical techniques. Such techniques include the step of bringing into association the active ingredients with the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations of the present invention suitable for oral administration may be presented as descrete units such as capsules, cachets or tablets each containing predetermined amounts of the active ingredients; as powders or granules; as solutions or suspensions in an aqueous liquid or a non-aqueous liquid; or as oil-in-water emulsions or a water-in-oil liquid emulsions. A tablet may be made by compression or moulding, optionally with one or more accessory ingredients. Compressed tablets may be prepared by compressing in a suitable machine the active ingredients in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

For infections of the eye or other external tissues, e.g., mouth and skin, the formulations are preferably applied as a topical ointment or cream containing the antiviral active ingredient in an amount of, for example, 0.075 to 20% w/w, preferably 0.2 to 15% w/w and most preferably 0.5 to 10% w/w. When formulated in an ointment, the active ingredients may be employed with either paraffinic or a water-miscible ointment base. The active ingredients also may be formulated in a cream with an oil-in-water cream base. Alternatively, the antiviral compound may be administered topically while the nucleoside transport inhibitor is administered separately by another route (e.g., orally, rectally, intravenously, subcutaneously or intramuscularly). If desired, the aqueous phase of the cream base may include, for example, at least 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulation may desirably include a compound which enhances absorption or penetration of the active ingredient through the skin or other affected areas. Examples of such dermal penetration enhancers include dimethylsulphoxide and related analogues.

The oily phase of the emulsions of this invention may be constituted from known ingredients in known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulsifiers and emulsion stabilizers suitable for use in the formulation of the present invention includet Tween 60, Span 80, cetostearyl alcohol, myristyl alcohol, glyceryl mono-stearate and sodium lauryl sulphate.

The choice of suitable oils or fats for the formulation is based on achieving the desired cosmetic properties, since the solubility of the active compound in most oils likely to be used in pharmaceutical emusion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl sterate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredient. The antiviral active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavoured basis, usually sucrose and acacia or tragacanth; pastilles comprising the active ingredient in an inert basis such as gelatin and glycerine, or sucrose and acacia; and mouth washes comprising the active ingredients in a suitable liquid carrier. Formulations for rectal administration may be presented as a suppository with a suitable base comprising for example cocoa butter or a salicylate. Formulations suitable for nasal administration wherein the carrier is a solid include a coarse powder having a particle size, for example, in the range 20 to 500 microns which is administered in a manner in which snuff is taken, i.e., by rapid inhalation through the nasal passage from a container of the powder held close up to the nose. Suitable formulations wherein the carrier is a liquid for administration as, for example, a nasal spray or as nasal drops, include aqueous or oil solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described. Preferred unit dosage formulations are those containing a daily dose or unit daily sub-dose, as herein above recited, or an appropriate fraction thereof, of the active ingredients.

It should be understood that in addition to the ingredient particularly mentioned above the formulations of this invention may include other agents conventional in the art having regard to the type of formulation in question, for example, those suitable for oral administration may include flavouring agents.

ANTIVIRAL ACTIVITY (1) Examples of the activity against herpes simplex virus of dilazep, dipyridamole and 6-[(4-nitrobenzyl)thio]-9-($\beta$-D-ribofuranosyl)purine (compound A) and Acyclovir (ACV), and combinations of ACV with each of the foregoing nucleoside transport inhibitors are shown in Table 1.

The antiviral activity was determined using a plaque reduction assay. Petri plates were seeded with Vero cells which were then allowed to grow to confluency. Each plate was then infected with a fixed number of plaque forming units (about 100–500) of herpes simplex type 1 (KOS strain). The inhibitors, either alone or in the indicated combinations, were dissolved to give the indicated concentrations in minimal essential medium containing 2% heat inactivated fetal calf serum and 0.5% human immune serum globulin. One hour after infection the solutions (10 ml per plate) were added to the cultures. Three days later the cultures were formalin-fixed and stained with crystal violet, and the plaques were counted.

TABLE 1

| Inhibitor | Conc. ($\mu$M) | Average Plaque Count | % Inhibition |
| --- | --- | --- | --- |
| ACV | 1.0 | 279.5 | 41.8 |
|  | 2.5 | 133.5 | 72.3 |
|  | 5.0 | 29.5 | 93.8 |
| Dilazep | 1.0 | 442.0 | 8.0 |
| Dipyridamole | 5.0 | 474.0 | 1.0 |
| Compound A | 2.0 | 484.0 | 0 |
| Dilazep/ACV | 1.0/1.0 | 88.5 | 81.5 |
|  | 1.0/2.5 | 12.5 | 97.4 |
|  | 1.0/5.0 | 1.0 | 99.8 |
| Dipyridamole/ACV | 5.0/1.0 | 100.0 | 79.2 |
|  | 5.0/2.5 | 9.0 | 98.1 |
|  | 5.0/5.0 | 2.0 | 99.6 |
| Compound A/ACV | 2.0/1.0 | 211.0 | 56.0 |
|  | 2.0/2.5 | 27.5 | 94.3 |
|  | 2.0/5.0 | 0 | 100.0 |

Average number of plaques in controls = 480.

The following examples serve to further illustrate the present invention.

PHARMACEUTICAL FORMULATIONS

In the following Examples, the antiviral compound is acyclovir and the nucleoside transport inhibitor is dilazep.

EXAMPLE 1

| Tablet | Weight (mg) |
| --- | --- |
| Nucleoside Transport Inhibitor | 300 |
| Antiviral Compound | 200 |
| Lactose | 105 |
| Starch | 50 |
| Polyvinylpyrrolidinone | 20 |
| Magnesium Sterate | 10 |
|  | 685 |

Mix the active compounds with the lactose and starch and wet granulate with a solution of the polyvinylpyrrolidinone. Dry, sift, blend the granules with magnesium stearate and compress.

EXAMPLE 2

| Capsule | Weight (mg) |
| --- | --- |
| Nucleoside Transport Inhibitor | 300 |
| Antiviral Compound | 200 |
| Lactose | 100 |
| Sodium Starch Glycollate | 10 |
| Polyvinylpyrrolidinone | 10 |
| Magnesium Stearate | 3 |
|  | 623 |

Mix the active compounds with the lactose and sodium starch glycollate and wet granulate with a solution of the polyvinylpyrrolidinone. Dry, sift, blend the granules with the magnesium stearate and fill into hard gelatin capsules.

EXAMPLE 3

| Cream | Weight |
| --- | --- |
| Nucleoside Transport Inhibitor | 7.5 g |
| Antiviral Compound | 5.00 g |
| Glycerol | 2.00 g |
| Cetostearyl alcohol | 6.75 g |

| Cream | Weight |
| --- | --- |
| Sodium Lauryl Sulphate | 0.75 g |
| White Soft Paraffin | 12.50 g |
| Liquid Paraffin | 5.00 g |
| Chlorocresol | 0.10 g |
| Purified Water to | 100.00 g |

Dissolve the active compounds in a mixture of purified water and glycerol and heat to 70° C. Heat the remaining ingredients together at 70° C. Add the two parts together and emulsify. Cool and fill into containers.

EXAMPLE 4

| Intravenous Injections | Amount |
| --- | --- |
| (1) Antiviral Compound | 200 mg |
| Nucleoside Transport Inhibitor | 300 mg |
| Glycerol | 200 mg |
| Sodium Hydroxide solution qs | pH 7.0–7.5 |
| Water for Injections to | 10 ml |

Method: Add the glycerol to some of the Water for Injections. Dissolve the two active compounds and adjust the pH with Sodium Hydroxide solution. Make up to volume with additional Water for Injections. Under aseptic conditions, sterilize the solution by filtration, fill into sterile ampoules and seal the ampoules.

| (2) Antiviral Compound | 100 mg |
| --- | --- |
| Nucleoside Transport Inhibitor | 150 mg |
| Sodium Hydroxide solution qs to | pH 8.0–9.0 |
| Mannitol | 125 mg |
| Water for Injections to | 2.5 ml |

Method: Dissolve the active compounds and the mannitol in a part of the Water for Injections. Adjust the pH with the sodium hydroxide solution and make up to volume with additional Water for Injections. Under aseptic conditions, sterilize with solution by filtration, fill into sterile vials and remove the water by freeze-drying. Seal the vials under an atmosphere of nitrogen and close the vials with a sterile closure and metal collar.

TOXICITY

The $LD_{50}$ values for acyclovir, dilazep and dipyridamole, referred to above are as follows:

| Compound | $LD_{50}$ (mg/kg) |
| --- | --- |
| Dilazep | 3740 (male mice, oral) |
| Dipyridamole | 8400 (rats, oral) |
| Acyclovir | >10,000 (mice oral) |

What is claimed is:
1. A pharmaceutical formulation comprising dipyridamole and acyclovir, the amounts of dipyridamole and acyclovir being present in amounts to provide a synergistic antiviral effect.

* * * * *